United States Patent
Angelo, Jr.

[11] Patent Number: 5,674,074
[45] Date of Patent: Oct. 7, 1997

[54] PERIODONTAL PROCEDURE

[76] Inventor: Patrick J. Angelo, Jr., 722 N. Prospect, Park Ridge, Ill. 60068

[21] Appl. No.: 405,547

[22] Filed: Jun. 13, 1996

[51] Int. Cl.⁶ .................................................. A61C 5/00
[52] U.S. Cl. ........................................................ 433/215
[58] Field of Search ................................. 423/215, 216

[56] References Cited

U.S. PATENT DOCUMENTS

| | | | |
|---|---|---|---|
| 5,006,071 | 4/1991 | Carter | 433/215 |
| 5,093,179 | 3/1992 | Scantlebury et al. | 433/215 X |
| 5,418,221 | 5/1995 | Hammarstrom et al. | 433/215 X |
| 5,455,041 | 10/1995 | Genco et al. | 433/215 X |

*Primary Examiner*—Nicholas D. Lucchesi
*Attorney, Agent, or Firm*—Brezina & Ehrlich

[57] ABSTRACT

A novel periodontal procedure for performing periodontal treatment including the steps of applying anesthetic to the area to be treated and making an incision on the facial side of the most posterior tooth and continuing the incision toward the most anterior tooth. The incision begins at the distal facial line angle of the most posterior tooth on the facial side of the arch and is made at about a forty-five degree angle to the plane of the tooth, forming an inverse bevel within the coronal portion of the pocket. A similar incision is made on the lingual side in the same manner. The incision is reentered to separate the facial, lingual, and papillary tissues from the underlying connective tissue so that the separated facial, lingual, papillary tissue may be removed, thereby removing the coronal portion of the tissue pocket and initially exposing root surfaces. The remaining tissue pocket is then removed. Soft tissue tags adjacent to the incised areas are also removed. Next, gross bacterial accretions on the root surface are removed followed by fine bacterial accretion removal. Post-treatment procedures to aid healing include light scaling of the teeth in the treated area followed by polishing of the teeth in the treated area with fluoride prophylaxis material and applying about a 30% trichloracetic acid to the facial, lingual, and proximal areas about seven days after treatment. The post-operative procedure is repeated seventeen days and thirty-one days after treatment.

13 Claims, 5 Drawing Sheets

80
82

PERIODONTAL PROCEDURE

BACKGROUND OF THE INVENTION

With the advent of soft tissue gum management and the Periodontal Screening and Recording System (PSR), many dental practitioners have become increasingly aware of patients having generalized five to six millimeter pocket depths which bleed, may exhibit exudate in response to gentle probing, and may exhibit horizontal bone loss. Unfortunately, even after conventional soft tissue gum management has been completed, bacterial accretions may still exist on root surfaces. Further attachment loss is risked due to the episodic destructive characteristics of periodontal disease when bacteria remains on the root surface.

This situation may also be present in patients regressing after conventional flap surgery. The chances of removing all bacteria from the root surfaces even in pockets only three to five millimeters deep through standard scaling and root planing are not predictable. In fact, the success rate may be less than 50%. The inability to remove accretions in horizontal bone loss furcations or concavities further complicates successful therapy.

Historically, curettage with scaling and root planing, gingivectomy, and gingivoplasty, and various flap procedures have been utilized to remove bacterial accretions and decrease periodontal pocket depths. Curettage with scaling and root planing does not ensure that residual plaque and calculus are removed from the treated surfaces. Sutures may be needed, depending on fragility of the tissue and the aggressiveness of the curettage.

Gingivectomy procedures allow treatment of suprabony pockets through the removal of excessive gingival tissue utilizing a reverse bevel incision, but leaves a broad wound. Gingivoplasty, which is often done in conjunction with gingivectomy procedures, produces a broader, deeper wound than gingivectomy alone. Post-operative recovery can be both painful and slow. The initial step of the gingivectomy is to measure the base of the pocket with a pocket marker or a periodontal probe with a series of bleeding points. The bleeding points are crudely punctured on the outside of the gingiva to outline the location for the initial incision. These methods are tedious, time consuming, and often inaccurate if the pocket marker or probe is tilted, even slightly. An incorrect measurement, most likely, will result in an incision that may be too deep, thus, producing a more aggressive and larger wound, or may result in an initial incision that is too shallow.

In typical gingivectomy procedures, an initial incision is made apical to the bleeding points with a gingivectomy knife, such as with a Kirkland or Orban knife. This incision produces an external bevel made forty-five degrees relative to the tooth surface. The incision usually ends at the depth apical to the epithelial attachment. A bevel is placed on the tissue farthest from the tooth and is then lengthened to eliminate a plateau which would make the wound larger.

Use of an reverse bevel incision causes a broad and traumatic wound. The apical area of the epithelium attachment need not be removed to gain access to the root structure and subsequent bacterial debris. Tissue removal may be accomplished with heavy scalers, hoes or curettes, while removal of bacterial debris from the tooth surfaces is accomplished with smaller scalers and curettes. Final contour of the tissue is completed using a coarse diamond bur or a broad bladed knife. Finally, a large dressing is placed over the entire wound area.

These procedures require application of an uncomfortable surgical dressing due to the broad wound. In a majority of gingivectomy surgeries, a gingivoplasty is performed which reshapes the gingiva to achieve physiologic contours. This is performed with sharp periodontal knives in a scraping motion on the surface of the gum or with a coarse diamond rotary bur abrading the surface of the gingiva. Both the periodontal knife and coarse diamond burs leave deep wounds resulting in delayed healing, increased post-operative pain, and an increased chance of bleeding. With gingivectomy procedures, maxillary anterior esthetics are severely compromised due to gross removal of facial tissue of the affected teeth.

Alternatively, gingival flap procedures expose bone which generally, will be partially resorbed depending on the thinness of bone and the length of time that the gingival flap is raised. Furthermore, flap procedures which are typically performed on deeper pockets with bleeding on probing and vertical bone loss, require a high degree of skill and may cause the patient moderate to severe pain, swelling, and discoloration. Additionally, suturing is required. In flap surgery, the gum is separated from the tooth to expose the root surface and bone. Then, the separated flaps of gum are sutured back to each other in between each tooth after debridement has been completed.

SUMMARY OF THE INVENTION

The need for a more conservative procedure to gain visual access to the root surface affects a large number of existing patients. The inventive periodontal procedure according to the present inventive method substantially overcomes the above problems. The inventive periodontal procedure provides greater access to the root surface than scaling and root planing, is less invasive than flap procedures, and is less traumatic than a standard gingivectomy with or without accompanying gingivoplasty.

Periodontal disease is site specific. Accordingly, the periodontal procedure is a site-specific procedure. Many patients with generalized five to six millimeter pockets who bleed and may exhibit exudate in response to gentle probing are more likely to have the destructive pattern of periodontal disease.

The inventive periodontal procedure is an alternative to flap procedures or gingivectomy procedures. The patient's bony pattern (i.e., horizontal or vertical), rather than the amount of bone loss, must be considered. Patients most likely to benefit from conservative access therapy are those with symptoms of chronic adult periodontitis which results in episodic attachment loss. The present periodontal procedure may stop the progression of attachment loss in areas where regressing pockets of generalized five to six millimeters in depth where bleeding upon gentle probing and horizontal bone loss are evident. The clinical objective is to gain visual access to the root surface while causing minimum trauma to the patient.

This procedure is contraindicated in patients having mucogingival defects, severe hyperplastic tissue, vertical bone loss, and deep pocketing on the facial aspects of the maxillary anterior sextant. In the absence of such contraindications, the novel periodontal procedure offers many advantages over flap procedures, or standard gingivectomy such as less traumatic complete access to subgingival bacterial accretions, reducing pockets to facilitate patient maintenance, minimal patient trauma and bleeding, decreased post-operative discomfort, no swelling of the jaw, and no discoloration of the facial tissues. The advantage versus scaling is predictability of pocket reduction to facilitate patient maintenance due to predictable elimination of bacterial accretions.

The periodontal procedure includes the steps of applying local anesthetic to the area to be treated and making an incision on the facial side of the most posterior tooth and carrying the incision anteriorly. The lingual aspect in treated in the same manner. The incision begins at the distal facial line angle of the most posterior tooth of the arch and is made optimally at about a forty-five degree angle to the plane of the tooth forming an inverse bevel. The tip of the cutting instrument remains within the sulcus. In areas of the mouth where it is difficult to maintain the forty-five degree angle if the tissue is thin, the practitioner may vary the range from between zero to forty-five degrees. The incision should never be a reverse bevel such as is used in the standard gingivectomy. The incision is reentered at the same inverse forty-five degree angle to separate the facial, lingual, and papillary tissues from underlying connective tissue so that the separated tissue may be removed, thereby removing the coronal portion of the tissue pocket and initially exposing the root surface. The removal may be performed with a curved mosquito hemostat or other hand instruments. The tip of the tissue scissors then rides the base of the pocket and is angled at about a forty-five degree inverse bevel. The remaining pocket and all soft tissue tags attached to the incised area are then removed. This step insures the vision to the clinical apical portion of the pocket thus providing access to bacterial accretions. Next, gross and fine bacterial accretions and bacterial endotoxins on the root surface are removed. Application of 30% trichloracetic acid (TCA) to the facial, lingual, and proximal tissues is then performed.

Post-treatment procedures to aid healing include, at the seven day period, light scaling of the treated area, polishing of the treated area with fluoride prophylaxis material, and application of 30% TCA to the facial, lingual, and proximal tissues. After about seventeen days following treatment, light scaling of the treated area is again performed followed by polishing of the treated area with fluoride prophylaxis material and application of the 30% TCA. Finally, after about thirty-one days after treatment, light scaling of the treated area is performed and the treated area is again polished with fluoride prophylaxis material followed by application of 30% TCA.

The inventive periodontal procedure results in cessation of the destructive cycle of periodontal disease by gaining access to the bacteria on the root surfaces for removal thereof. This procedure is advantageous for several reasons. The patient has an alternative treatment that can be easier for the patient to understand when explained by the clinician. The hygienist is easily and efficiently incorporated into the team approach of diagnosing. The general dentist who now performs flap surgery also has an alternative treatment. The patient may be referred to a periodontist sooner if the general dentist understands that a more conservative procedure may be performed. This results in an enhanced prognosis. This novel periodontal procedure may lower dental care costs by reducing the need for expensive and intricate flap surgeries or for dental specialists who typically perform more invasive and expensive procedures. The periodontal procedure allows the general dental practitioner to more readily perform periodontal treatment at a reduced cost to the patient.

The periodontal procedure may resolve the problem of gaining visual access to bacteria using a more conservative approach than gingivectomy and various flap surgery techniques. The novel periodontal procedure is a non-flap procedure with no reflection of tissue from the tooth. It does not expose bone, does not require sutures, and the patients can heal with less post-operative discomfort absent swelling or discoloration.

BRIEF DESCRIPTION OF THE DRAWINGS

The features of the present invention which are believed to be novel are set forth with particularity in the appended claims. The invention, together with further objects and advantages thereof, may best be understood by reference to the following description in conjunction with the accompanying drawings.

DETAILED DESCRIPTION OF THE INVENTION

Figure 1:
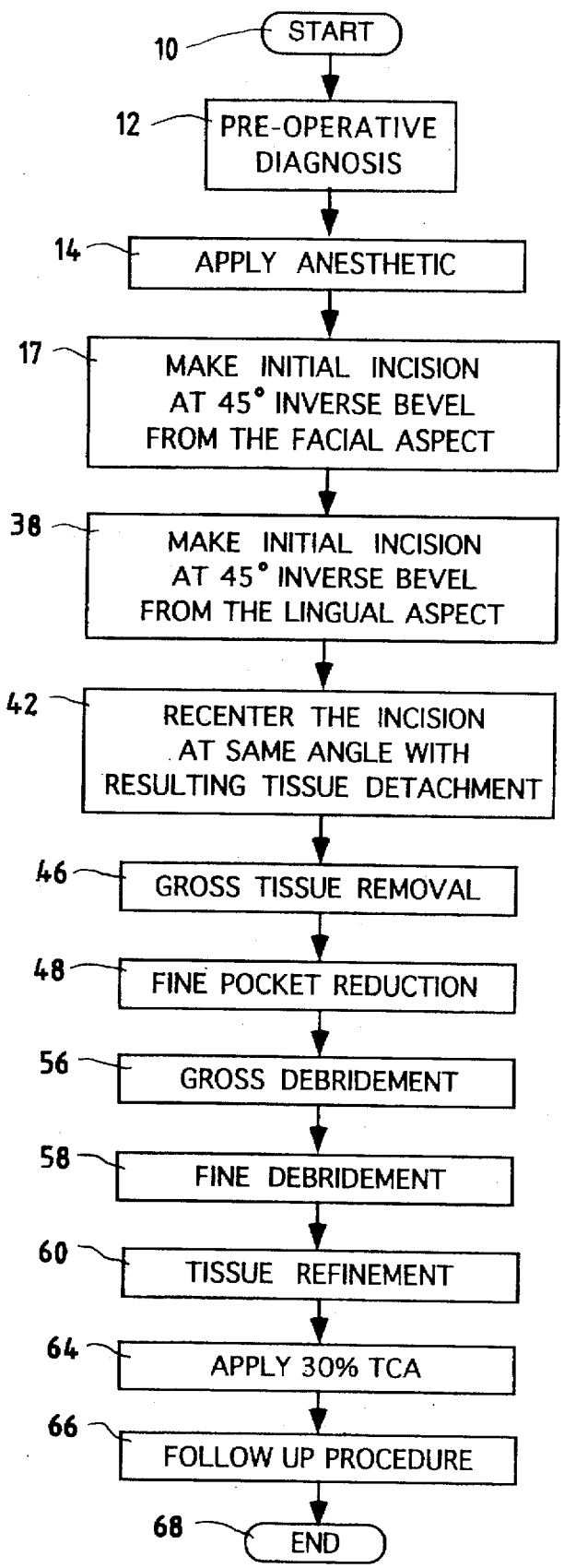
FIG. 1 shows a flowchart depicting the steps involved according to the inventive method.

Referring now to FIG. 1, step 10 shows the start of the method. Initially, a pre-operative diagnosis must be made indicating application of the above-described inventive method, as shown in step 12. Once such a pre-operative diagnosis is made, the clinical step of applying local anesthetic, as illustrated in step 14 is performed.

Adequate local anesthetic is a prerequisite. Administration of mepivacaine 2% (Carbocaine) with Neo-cobefrin 1:20,000 has been found useful. Papillary hemostasis is provided by injecting both the lingual and facial aspects with 2% lidocaine (Xylocaine) with epinephrine 1:50,000 or 1:100,000, or bupivacaine (Marcaine) with epinephrine 1:200,000, depending on the individual patient's reaction to epinephrine.

Figure 2A:
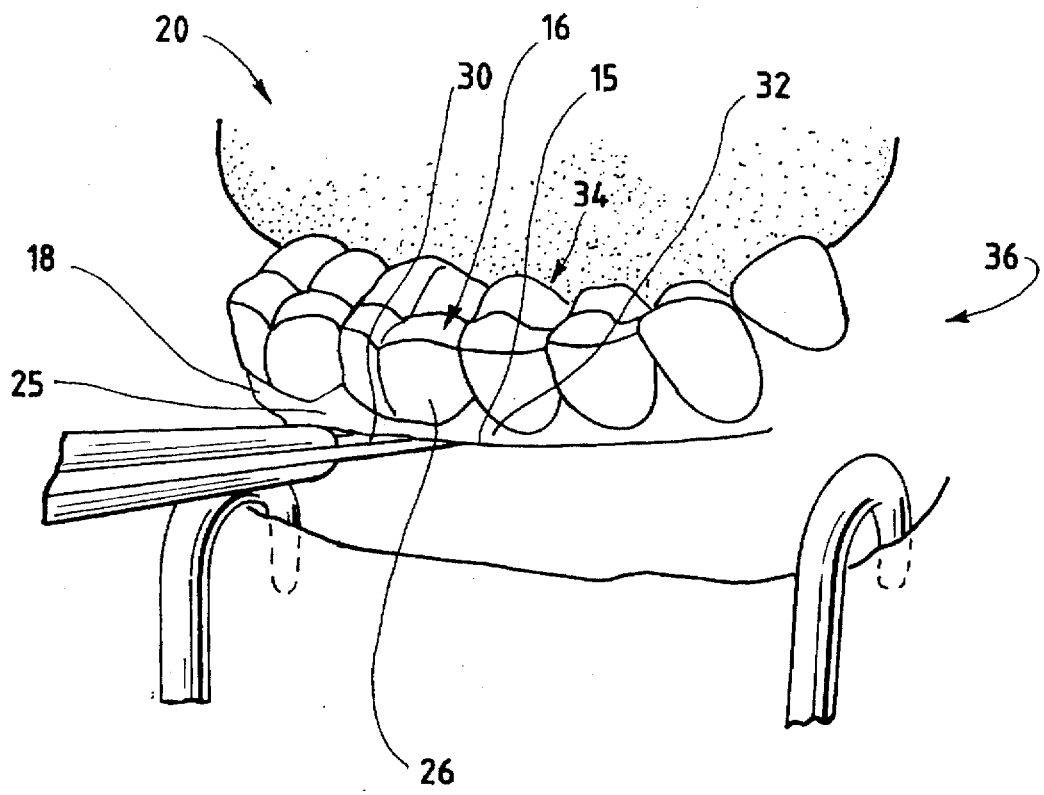
FIG. 2a is a drawing depicting an incision made at an inverse forty-five degree angle according to the inventive method.
Figure 2B:
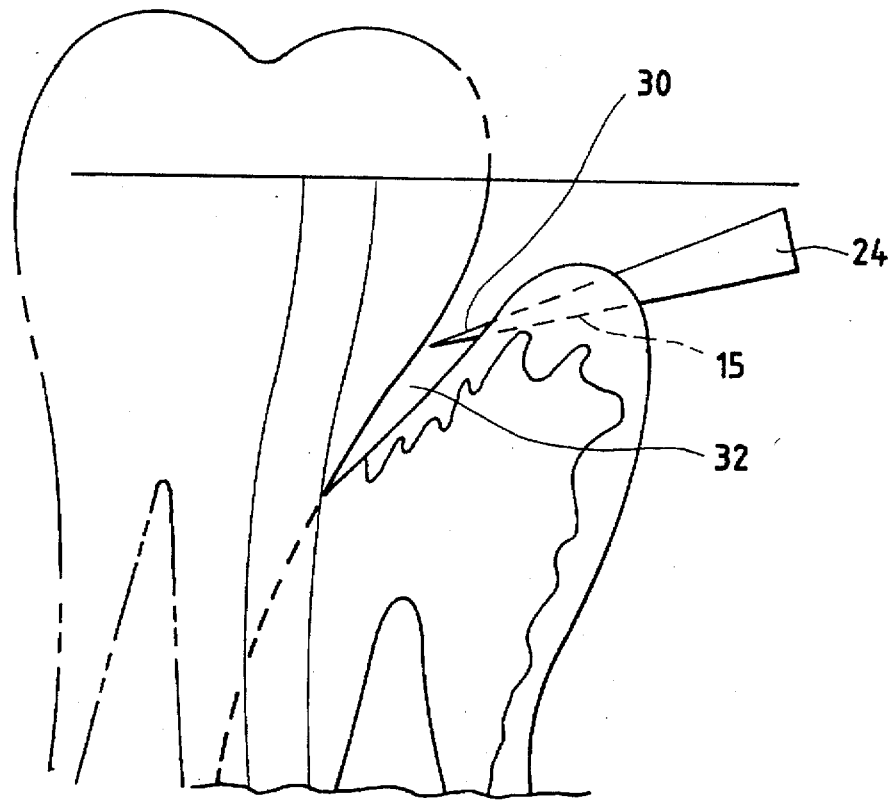
FIG. 2b is a drawing depicting the tip of a blade remaining in the sulcus.

Referring now to FIGS. 1, 2a, and 2b, an incision 15 is made relative to the facial aspect 16, as shown in step 17 of FIG. 1. Beginning at the distal facial line angle 18 of the most posterior tooth 20 in the arch, the incision 15 is made at a forty-five degree inverse bevel using an instrument such as a No. 15 Bard Parker blade 24. However, any suitable blade may be used. Note that the angle designated as 25 is elevated forty-five degrees relative to the plane 26 of the teeth in an inverse manner.

The incision 15 is carried anteriorly to include the papilla and approximately one to one and one-half millimeters of facial tissue. The tip 30 of the blade remains within the sulcus 32 as the incision is made. This process continues until the facial aspect 16 and papilla are incised using the forty-five degree inverse beveled procedure.

Next, the lingual aspect 34 is incised using the above-described procedure, as shown in step 38. If two millimeters or less of keratinized gingiva exists, only the papilla in that area is excised. Now, the tissue is ready to be detached.

Figure 3:
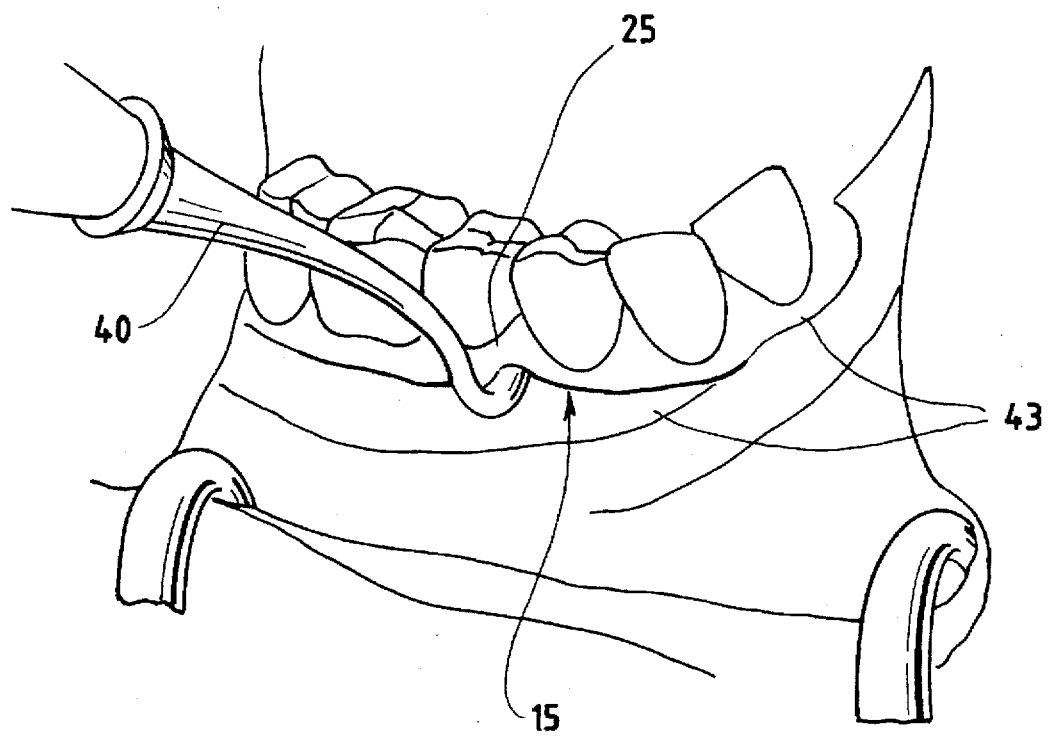
FIG. 3 is a drawing depicting separation of facial papillary tissues from the underlying connective tissue according to the inventive method.

Referring now to FIGS. 1 and 3, the incision 15 is reentered with an instrument 40 at the same forty-five degree inverse angle 25 as was made by the initial incision. The instrument 40 may be a No. 1/2 Orban knife, however any suitable instrument may be used, as shown in step 42 of FIG. 1. This is done to ensure that the facial, lingual, and papillary tissues are devoid of attachment to the underlying connective tissue 43.

Figure 4:
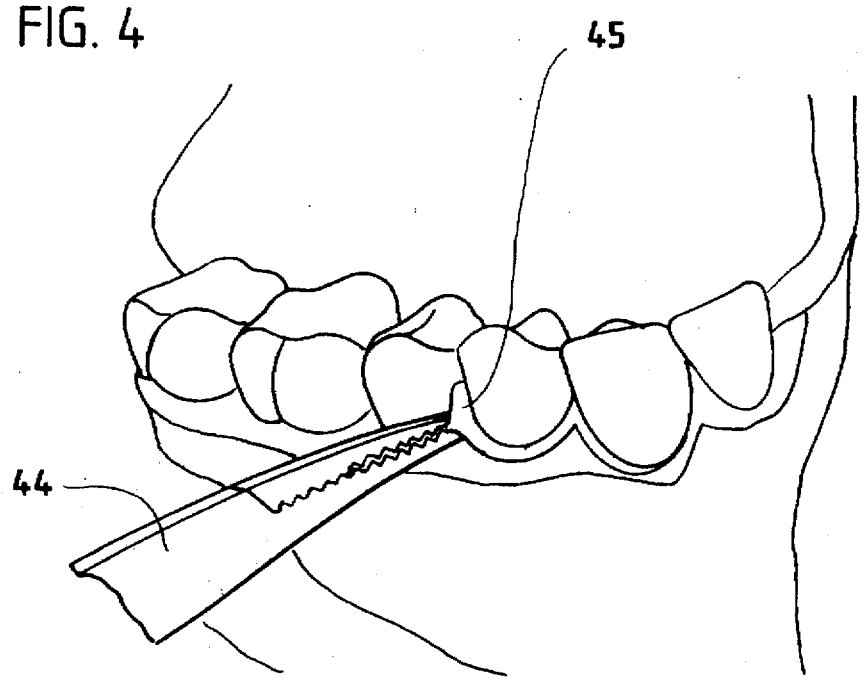
Fig. 4 is a drawing depicting removal of the separated facial papillary tissue from underlying connective tissue according to the inventive method.

Referring now to FIGS. 1 and 4, gross tissue removal using a hemostat 44 removes the detached tissue 45, as shown in step 46. However, any suitable instrument may be used.

Figure 5:
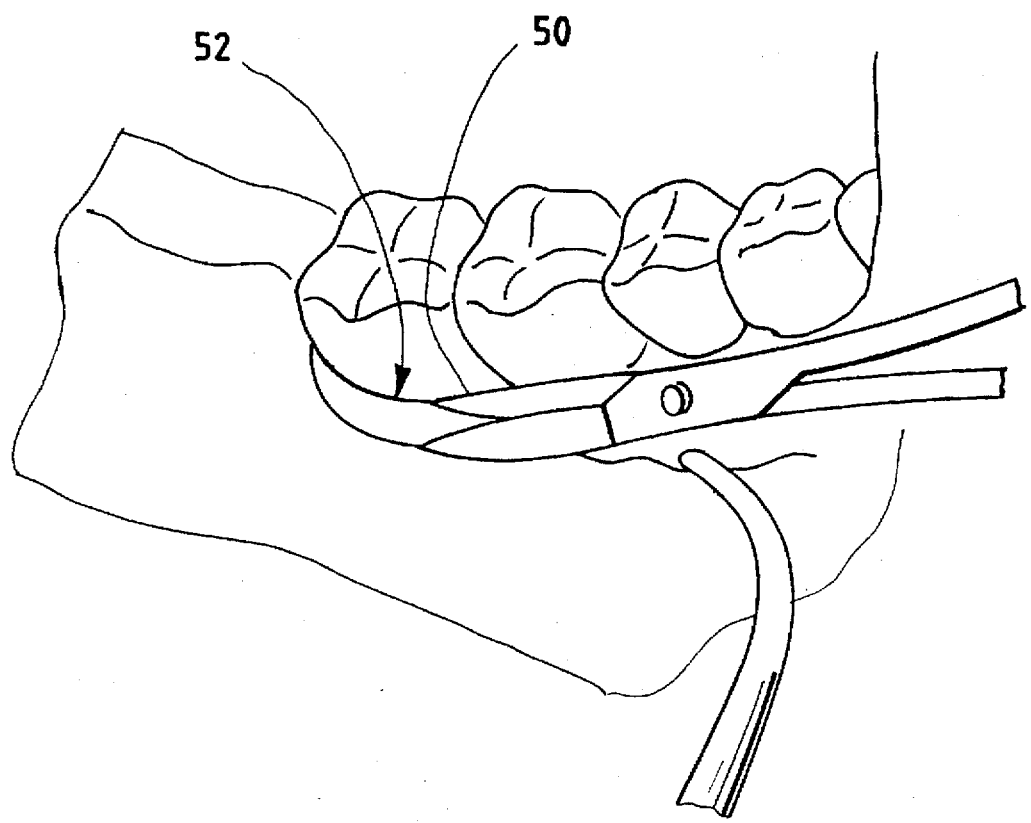
FIG. 5 is a drawing depicting the tip of the tissue scissors at the base of the tissue pocket.
Figure 6:
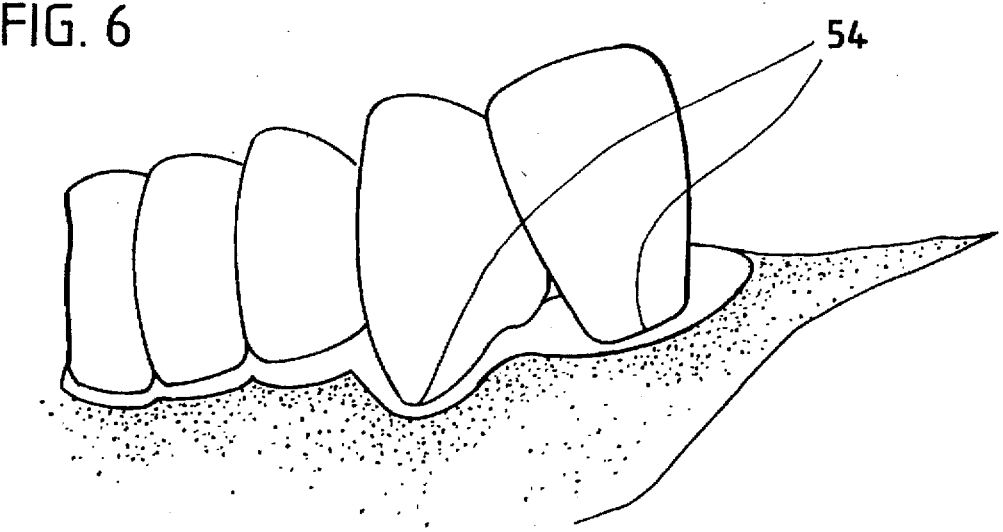
FIG. 6 is a drawing depicting the exposed root after removal of the facial papillary tissue according to the inventive method.

Referring now to FIGS. 1 and 5, fine pocket reduction is shown in FIG. 5, as indicated in step 48 of FIG. 1. The tip of a tissue scissor 50 or other suitable instrument is placed into the remaining pocket 52 at the most apical point, while carefully maintaining the forty-five degree inverse angle. The remaining pockets 52 on the facial, lingual, and proximal regions are then removed and all soft tissue tags (not shown), if any, are removed. In essence, "riding the base of the pocket" with the tip of the scissors removes only the surrounding pocket and papillary gingival tissue. This step completes the site specific surgery for the site specific destructive disease. As shown in FIG. 6, the required tissue has been removed exposing the root surfaces 54 to obtain visual access to disease causing bacteria.

The next step is gross debridement of root surfaces, as illustrated in step 56. Since the bacterial accretions on the root surfaces 54 are now visually accessible, gross removal of the accretions may be performed with an ultrasonic scaler. However, any suitable device may be used including hand scaling instruments.

As shown in step 58, fine debridement of root surfaces 54 further removes the bacterial accretions from the root surfaces. This is performed with a hand scaler or non-end cutting bur. As shown in step 60, tissue refinement may be necessary, at the discretion of the clinician to remove any fine tissue tags making sure not to increase the width of the wound. This may be performed with either a No. 15 blade, a No. 1/2 Orban knife, a curette, or a tissue scissors. However, any suitable instrument may be used. Next, 30% TCA is applied to the facial, lingual, and proximal tissue as shown in step 64.

Due to the small size of the wound, periodontal dressing is not required. Alternatively, prescribing an antibiotic and nonsteroidal anti-inflammatory therapy may complete postoperative protocol. Chlorhexidine 0.12% (Peridex) rinsing twice per day to promote healing is prescribed during this appointment.

Figure 7:
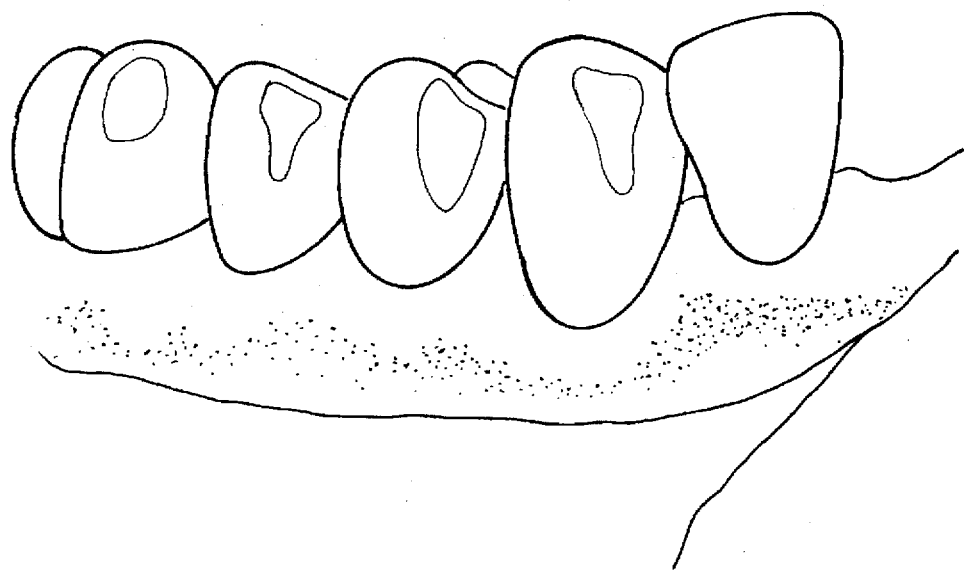
FIG. 7 is a drawing depicting post-operative healing according to the inventive method.

Referring now to FIGS. 1 and 7, throughout the follow-up period, beginning at 7 days as shown in step 66, the dentist and hygienist counsels the patient and reinforces oral hygiene techniques. A light ultrasonic or hand scaling of the surgical region is then performed. After scaling, the area is polished with fluoride prophylaxis paste followed by 30% TCA application to the facial, lingual, and proximal areas. The patient is then instructed to brush with fluoride toothpaste, to floss gently after each meal, and to rinse with a fluoride solution. Chlorhexidine 0.12% (Peridex) rinse is continued until one sixteen ounce bottle is completed.

Seventeen days after surgery, a light scaling is again performed followed by polishing with fluoride prophylaxis paste followed by TCA 30% application to the facial, lingual, and proximal surfaces. The patient is then instructed to use a rubber tip stimulator to further insure proper oral hygiene.

Thirty-one days after surgery, a light scaling of the surgical area is repeated followed by polishing with fluoride prophylaxis paste, followed again by TCA 30% application to the facial, lingual and proximal surfaces. The patient is further instructed to continue use of the fluoride toothpaste, floss, and the rubber tip stimulator and to brush subgingivally with Listerine®. After the follow-up procedures have been completed, the procedure is complete, as shown in step 68.

Figure 8:
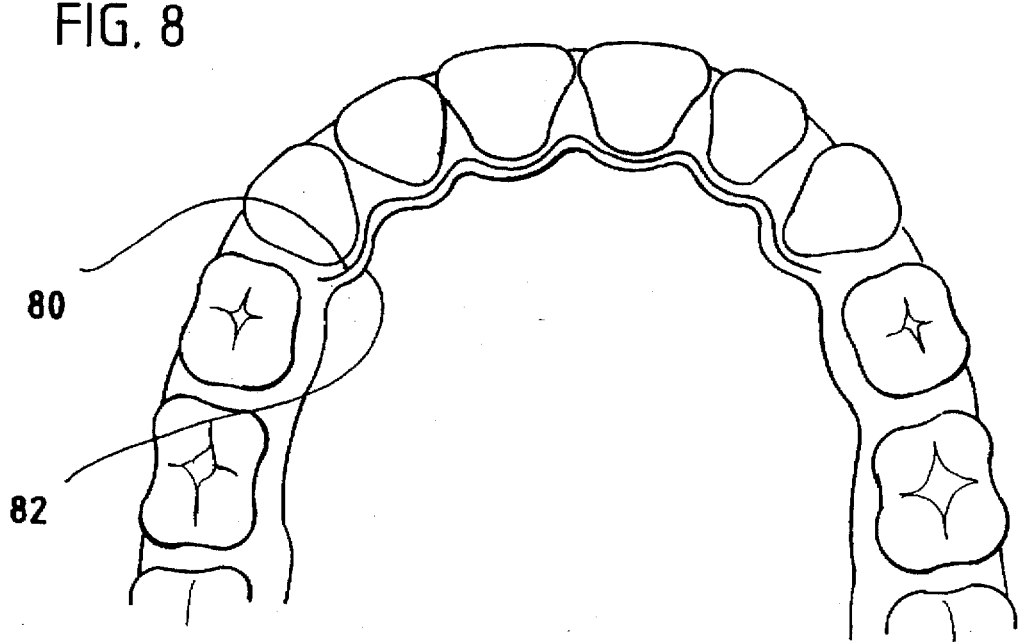
FIG. 8 is a drawing depicting incisions used in the maxillary anterior sextant of the papillary region.

Referring now to FIGS. 1 and 8, the above periodontal procedure, the steps of which are shown in FIG. 1, is indicated for use in the five sextants of the mouth. Steps 13 and 38 are modified for use in the maxillary anterior sextant. For aesthetic reasons, this sextant is treated from the palatal aspect. The facial tissue is not altered at anytime. In the maxillary anterior sextant, a second incision 80 is made sulcularly to include only the palatal one-half of the maxillary anterior papilla. The initial incision is identically performed on the palatal surfaces. The procedure is then identical from this point forward to the procedure performed in the remaining five sextants as described above, as indicated in steps 42 through 68. This allows access to the proximal bacterial accretions from the palatal aspect without altering the facial tissue, this resulting with the proper aesthetics.

CASE REPORT

In operation, the inventive periodontal procedure is effective, as shown by the following case study. The 51-year old patient was referred for periodontal consultation by her general dentist. Although she had undergone a course of soft tissue management, generalized pocket depths of five to six millimeters were recorded. Bleeding and exudate were seen in response to gentle probing, and radiographs showed horizontal bone loss.

Beginning at the distofacial line angle of the mandibular right second molar, a sterile No. 15 Bard Parker blade was used to make a forty-five degree inverse bevel incision with the tip of the blade remaining in the sulcus. The incision was continued anteriorly to include the papilla and approximately one to one and one-half millimeters of facial tissue. The lingual aspect was incised in a similar fashion. The incision was re-entered with the No. 1/2 Orban knife, giving careful attention to separating the mesial and distal connective tissue attachment of the papilla. The excised tissue was then removed with a hemostat. The tip of a tissue scissor was next used at the same inverse bevel forty-five degree angle to remove the remaining pocket and soft tissue tags on the affected root surfaces. The root surfaces were then completely debrided. No periodontal dressing was placed over the surgical site and the patient returned for follow-up appointments and was treated as described above. Postoperative healing was uneventful. At the thirty-one day post-operative appointment, it was evident that the five to six millimeter pockets had been replaced by one to two millimeter healthy sulci.

A specific embodiment of the periodontal procedure according to the present inventive method has been described for the purpose of illustrating the manner in which the method may be used. It should be understood that implementation of other variations and modifications of the method and its various aspects will be apparent to those skilled in the art, and that the method is not limited by the specific embodiment described. It is therefore contemplated to cover by the present method any and all modifications, variations, or equivalents that fall within the true spirit and scope of the basic underlying principles disclosed and claimed herein.

What is claimed is:

1. A method for performing periodontal treatment for removing gingival tissue pockets and to gain access to a root surface of at least one tooth of a series of teeth for removing bacterial accretions upon said one tooth, the method comprising the steps of:

applying anesthetic to an area to be treated;

making a first incision on the facial side of a most posterior tooth of the series of teeth and continuing the incision toward a most anterior tooth of the series of teeth;

said first incision beginning at the distal facial line angle of said most posterior tooth;

said first incision being made at about a forty-five degree angle to the plane of said most posterior tooth forming an inverse bevel;

making a second incision on the lingual side of the most posterior tooth and continuing the incision toward the most anterior tooth;

said second incision beginning at the distal lingual line angle of said most posterior tooth;

said second incision being made at about forty-five degree angle to the plane of said most posterior tooth, forming an inverse bevel;

re-entering said first incision to separate the facial papillary tissues from underlying connective tissue;

re-entering said second incision to separate the lingual papillary tissues from underlying connective tissue;

removing the separated facial and lingual papillary tissue thereby removing a coronal portion of the tissue pocket to initially expose the root surface;

using a tissue cutting instrument applied at about a forty-five degree angle to the tooth surface to find an apical extent of the tissue pocket;

removing soft tissue tags attached adjacent to the first and second incisions;

removing gross bacterial accretions on the root surface;

removing fine bacterial accretions on the root surface; and performing post-treatment procedures to aid healing.

2. The method of claim 1 wherein said incisions are performed with a blade having a tip, said tip remaining within the coronal (sulcus) portion of the tissue pocket for the length of the incisions.

3. The method of claim 1 wherein the steps of performing the incisions are performed using a scalpel blade.

4. The method of claim 1 wherein the steps of performing the incisions are performed using an Orban knife.

5. The method of claim 1 wherein the steps of reentering the incisions are performed using a No. 1/2 Orban knife at about a forty-five degree inverse bevel angle.

6. The method of claim 1 wherein the steps of removing said separated tissue are performed using a hemostat.

7. The method of claim 1 wherein the step of removing the soft tissue tags is performed using a cutting instrument.

8. The method of claim 1 wherein the step of removing gross bacterial accretions is performed using an ultrasonic scaler.

9. The method of claim 1 wherein the step of removing gross bacterial accretions is performed using a hand scaling instrument.

10. The method of claim 1 wherein the step of removing the fine bacterial accretions is performed using a non-end cutting bur.

11. The method of claim 1 further includes the step of applying about 30% trichloracetic acid to facial, lingual, and papillary tissues after the step of removing fine bacterial accretions is performed.

12. The method of claim 1 wherein the step of performing post-treatment procedures further includes the steps of:

performing light scaling of the teeth in the treated area after about seven days after treatment;

subsequently polishing the teeth in the treated area with fluoride prophylaxis material and applying about a 30% trichloracetic acid to the facial, lingual, and proximal tissues;

performing light scaling of the teeth in the treated area after about seventeen days after treatment;

subsequently polishing the teeth in the treated area with fluoride prophylaxis material and applying about a 30% trichloracetic acid to the facial, lingual, and proximal tissues;

performing light scaling of the teeth in the treated area after about thirty-one days after treatment; and subsequently polishing the teeth in the treated area with fluoride prophylaxis material and applying about a 30% trichloracetic acid to the facial, lingual, and proximal tissues.

13. The method of claim 1 further including the steps of making a sulcular incision including the palatal half of the maxillary anterior papilla to gain visual access to the proximal surfaces of the maxillary anterior sextant from the palatal aspect.

* * * * *